(12) United States Patent
Warnack

(10) Patent No.: US 9,381,327 B2
(45) Date of Patent: Jul. 5, 2016

(54) BALLOON CATHETER

(71) Applicant: Abbott Laboratories, Abbott Park, IL (US)

(72) Inventor: Boris Warnack, Rangendingen (DE)

(73) Assignee: ABBOTT LABORATORIES, Abbott Park, IL (US)

( * ) Notice: Subject to any disclaimer, the term of this patent is extended or adjusted under 35 U.S.C. 154(b) by 146 days.

(21) Appl. No.: 13/784,820

(22) Filed: Mar. 4, 2013

(65) Prior Publication Data

US 2013/0184643 A1 Jul. 18, 2013

Related U.S. Application Data

(63) Continuation of application No. 11/429,508, filed on May 5, 2006, now Pat. No. 8,388,599.

(51) Int. Cl.
*A61M 25/10* (2013.01)
*A61M 25/01* (2006.01)

(52) U.S. Cl.
CPC ........... *A61M 25/1011* (2013.01); *A61M 25/10* (2013.01); *A61M 2025/0183* (2013.01); *A61M 2025/1013* (2013.01); *A61M 2025/1075* (2013.01)

(58) Field of Classification Search
CPC ........... A61M 25/10; A61M 25/1011; A61M 25/1018; A61M 2205/1013; A61M 2205/1088; A61M 2205/1085; A61M 2205/0183
USPC ............. 604/101.01, 101.02, 103.03, 103.07, 604/103.11, 103.13, 96.01
See application file for complete search history.

(56) References Cited

U.S. PATENT DOCUMENTS

| | | | |
|---|---|---|---|
| 4,963,133 A | 10/1990 | Whiple | |
| RE33,561 E | 3/1991 | Levy | |
| 5,253,759 A * | 10/1993 | Gouge et al. | 206/524.7 |
| 5,358,487 A * | 10/1994 | Miller | 604/103.11 |
| 5,447,497 A * | 9/1995 | Sogard et al. | 604/101.02 |
| 5,797,877 A * | 8/1998 | Hamilton et al. | 604/96.01 |
| 5,980,531 A * | 11/1999 | Goodin et al. | 623/1.11 |
| 6,096,056 A * | 8/2000 | Brown | 606/194 |
| 6,123,712 A * | 9/2000 | Di Caprio et al. | 606/108 |
| 8,388,599 B2 * | 3/2013 | Warnack | 604/509 |
| 2007/0038245 A1* | 2/2007 | Morris et al. | 606/213 |
| 2008/0051706 A1* | 2/2008 | Hirszowicz et al. | 604/103.03 |

FOREIGN PATENT DOCUMENTS

WO    WO20050102184    * 11/2005

OTHER PUBLICATIONS

John Olmsted et al., "Chemistry, the molecular science", William C. Brown Publishers, 2nd ed., p. 525-527 (1997).
www.en.wikipedia.org/wiki/polyamide, accessed on Apr. 6, 2012.
www.bpf.co.uk/plastipedia/polymers/polyamides.aspx, accessed on Apr. 6, 2012.

* cited by examiner

*Primary Examiner* — Andrew Gilbert
(74) *Attorney, Agent, or Firm* — Squire Patton Boggs (US) LLP

(57) ABSTRACT

A balloon catheter comprises a shaft having a proximal end and a distal end. An inflatable member is disposed adjacent the distal end of the shaft. The inflatable member has an inner inflatable member and an outer inflatable member disposed around the inner inflatable member. The inflatable members have different compliant properties.

9 Claims, 2 Drawing Sheets

BALLOON CATHETER

This application is a continuation of application Ser. No. 11/429,508, filed May 5, 2006, now U.S. Pat. No. 8,388,599, which is incorporated herein by reference.

BACKGROUND OF THE INVENTION

1. The Field of the Invention

The present invention relates generally to dilatation balloon catheters and systems used for expansion against an obstruction within a body vessel or channel, or to deliver devices such as, but not limited to, stents and therapeutic agents to sites within vascular or tubular channel systems of the body.

2. The Relevant Technology

The present invention relates to dilation balloon catheters employed applications such as percutaneous transluminal angioplasty (PTA) and percutaneous transluminal coronary angioplasty (PTCA) procedures, and more particularly to enhancements to such catheters and their dilatation balloons for improved maneuverability in smaller and more tortuous passages of the vascular system.

Dilatation balloon catheters are well known for their utility in treating the build-up of plaque and other occlusions in blood vessels. Typically a catheter is used to carry a dilatation balloon to a treatment site, where fluid under pressure is supplied to the balloon, to expand the balloon against an obstruction. Additionally, the expansion of the balloon may deploy a stent device in the treatment area.

The dilatation balloon usually is mounted along the distal end region of the catheter and surrounds the catheter. When the dilatation balloon is expanded, its main body portion or medial section has a diameter substantially larger than that of the catheter. Proximal and distal shafts or stems of the balloon have diameters substantially equal to the diameter of the catheter. Proximal and distal tapered sections, or cones, join the medial region to the proximal and distal shafts, respectively. Each cone diverges in the direction toward the medial region. Bonds between the balloon and catheter form a fluid tight seal to facilitate dilatation of the balloon by introduction of a fluid under pressure.

Along with body tissue compatibility, primary attributes considered in the design and fabrication of dilatation balloons are strength and pliability. A higher hoop strength or burst pressure generally reduces the risk of accidental rupture of a balloon during dilatation, although this is also dependent on the characteristics of the vessel lesion.

Pliability refers to formability into different shapes, rather than elasticity. In particular, when the balloon is an uninflated or deflated configuration, the dilatation balloon is evacuated, flattened and generally wrapped circumferentially about the catheter distal region. Thin, pliable dilatation balloon walls facilitate a tighter wrap that minimizes the combined diameter of the catheter and balloon during delivery. Furthermore, pliable balloon walls enhance the catheter "trackability" in the distal region, i.e. the capability to bend in conforming to the curvature in vascular passages.

One method of forming a strong and pliable dilatation balloon of polyethyleneterephthalate (PET) is disclosed in U.S. Pat. No. Re. 33,561 to Levy. A tubing of PET is heated at least to its second order transition temperature, and then drawn to at least triple its original length to axially orient the tubing. The axially orientated tubing is then radially expanded within a cylindrical form, to a diameter at least triple the original diameter of the tubing. The form defines the aforementioned main body, shafts and cones, and the resulting balloon has a burst pressure of greater than 200 psi.

Such balloons generally have a gradient in wall thickness along the cones. In particular, dilatation balloons with an expansion diameter in the range of 3.0-4.0 mm tend to have a wall thickness along the main body in the range of 0.0004-0.0008 inches (0.010-0.020 mm). Near the main body, the cones have approximately the same wall thickness. However, the wall thickness diverges in the direction away from the main body, until the wall thickness near each shaft is in the range of 0.001-0.0025 inches (0.025-0.063 mm). Smaller dilatation balloons (1.5-2.5 mm) exhibit the same divergence in the cone walls, i.e. from 0.0004-0.0008 inches near the main body to 0.0008-0.0015 inches (0.02-0.04 mm) near the associated shaft or stem.

The increased wall thickness near the stems does not contribute to balloon hoop strength, which is determined by the wall thickness along the balloon medial region. Thicker walls near the stems reduce maneuverability of the balloon and catheter. The dilatation balloon cannot be as tightly wrapped, meaning its delivery profile is larger, limiting the capacity of the catheter and balloon for treating occlusions in smaller vessels.

U.S. Pat. No. 4,963,133 to Noddin discloses an alternative approach to forming a PET dilatation balloon, in which a length of PET tubing is heated locally at opposite ends and subjected to axial drawing, to form two "necked down" portions which eventually become the opposite ends of the completed balloon. The necked down tubing is simultaneously axially drawn and radially expanded with a gas. The degree to which the tubing ends are necked down is said to provide control over the ultimate wall thickness along the tapered walls (or cones), so that the wall thickness can be equal to or less than the wall thickness along the main body. This approach, however, is said to result in a comparatively low burst pressure, only about 8 atmospheres, or about 118 psi.

Typically PCTA catheters can be classified as either having a compliant, semi-compliant or a non-compliant balloon. Compliance is defined as the increase in diameter from nominal balloon pressure to rated burst pressure. Non-compliant balloons have less than 7% increase in diameter. Semi-compliant balloon have between 7-10% increase in diameter and compliant balloons have at least 10% increase in diameter.

Typically a non-compliant balloon catheter is utilized first during most procedures and for very severe lesions. The non-compliant balloon catheter is used with high inflation pressure to crack calcified lesions. Subsequent to use of the non-compliant balloon catheter, a semi-compliant or a compliant balloon catheter may replace the non-compliant catheter for further vessel modeling.

Generally, the non-compliant balloon is used initially because of the balloons resistance to diameter growth, that is, very high pressure can be applied to the balloon without producing a significant diameter increase. A disadvantage of non-compliant balloon catheters is their inability to upsize a vessel. Upsizing is when a balloon is inflated at greater pressures causing the diameter to increase, for non-compliant balloons, upsizing is not possible because they are designed not to expand to a larger diameter at higher pressures. Thus, if the vessel needs to be upsized, the non-compliant balloon catheter must be removed from the vessel and a semi-compliant or compliant balloon catheter is then placed into the vessel.

Therefore there is a need for a balloon catheter having compliant, semi-compliant and non compliant properties.

BRIEF SUMMARY OF THE INVENTION

In accordance with the present invention there is provided a balloon catheter that can include a shaft having a proximal end and a distal end and an inflatable member disposed adjacent the distal end. The inflatable member can be a composite member having at least two separate inflatable members.

In accordance with the present invention there is provided a method of treating a vessel, the method including the steps of inserting a balloon catheter over at least a portion of a guidewire into a vessel or lumen, inflating a first inflatable member on the balloon catheter, deflating the inflatable member, and inflating another inflatable member, wherein the inflatable members are arranged in a coaxial fashion.

These and other objects and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only typical embodiments of the invention and are therefore not to be considered limiting of its scope. The invention will be described and explained with additional specificity and detail through the use of the accompanying drawings in which.

DETAILED DESCRIPTION OF THE PREFERRED EMBODIMENTS

Figure 1:
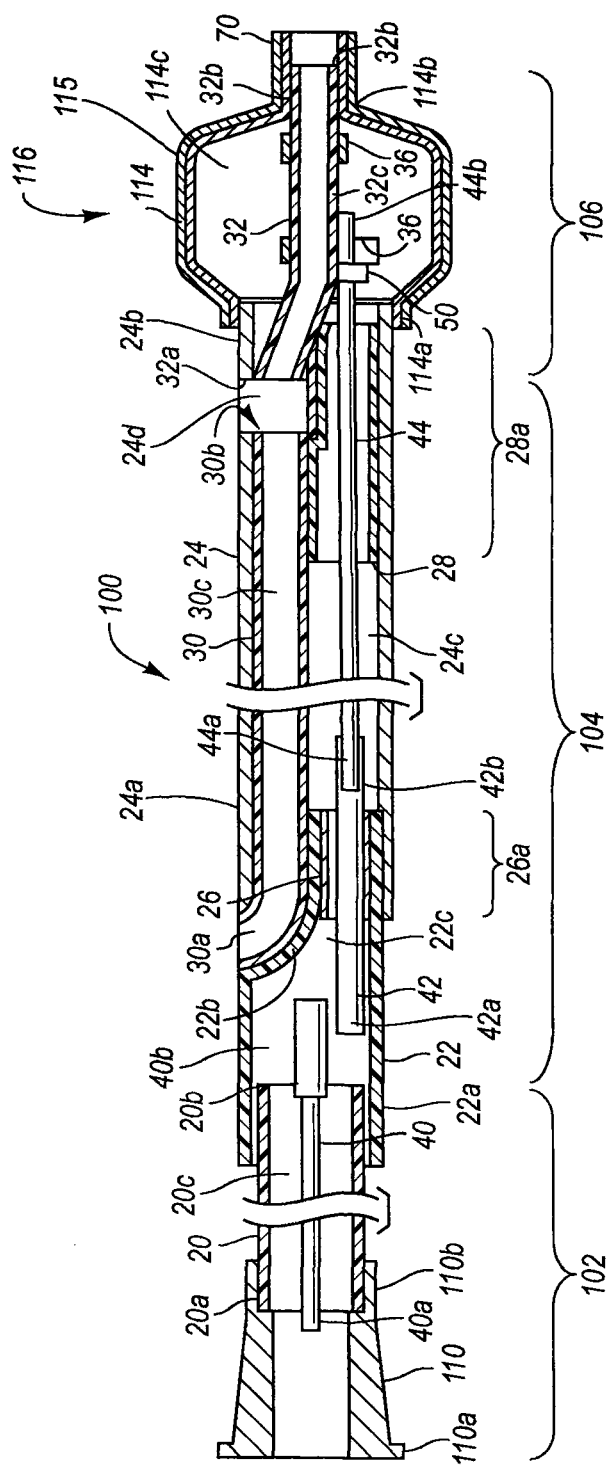
FIG. 1 is cross-sectional view of an exemplary embodiment of a catheter in accordance with the present invention.

While the present invention will be described with reference to a few specific embodiments, the description is illustrative of the invention and is not to be construed as limiting the invention. Various modifications to the present invention can be made to the embodiments by those skilled in the art without departing from the true spirit and scope of the invention as defined by the appended claims. It will be noted here that for a better understanding, like components are designated by like reference numerals throughout the various figures.

In accordance with the present invention there is provided a catheter for use in performing a medical procedure. The catheter in accordance with the present invention includes a shaft having a proximal end and a distal end and an inflatable member disposed radially about the shaft member, wherein the inflatable member can be configured to have different properties.

For purposes of illustration and not limitation, as embodied herein and as depicted in FIG. 1, catheter 100 has a main body portion including a proximal section 102, a distal section 106, and an intermediate section 104 disposed between the proximal and distal sections. Each section having a proximal end and a distal end.

Generally, the proximal section of the catheter 100 includes adapter 110 secured to proximal tubular member 20. Proximal tubular member 20 has a body including an outer surface, proximal end region 20a, distal end region 20b and inflation lumen 20c therebetween. Proximal end region 20a of proximal tubular member 20 is secured to adapter 110 by suitable structure or method. For example and not limitation, proximal tubular member can be affixed to adapter 110 by fusion, welding, overmolding, e.g., injection molding, shrinking, press fit or adhesive. Additionally, and as schematically depicted in FIG. 1, adapter 110 can have a distal end 110b in overlapping relation with a portion of proximal tubular member 20. Adapter 110 can be a hub or a handle, a manifold, or can be a luer fitting for connection with an inflation/deflation device, such as a syringe (not shown).

Proximal tubular member 20 can be made of any suitable material, such as metal, metal alloy, carbon, carbon reinforced materials, metal reinforced polymers, boron fiber reinforced materials, glass reinforced materials, aramid fiber reinforced materials, ceramic, composite, Kevlar, or polymer as described further below. The method of joining the adapter 110 and proximal tubular member 20 will depend on the materials used. In one configuration, proximal tubular member 20 further includes lumen 20c extending therethrough in fluid communication with adapter 110.

If desired, catheter 100 can include a strain relief (not shown), which extends from adapter 110 and is disposed along at least a portion of proximal tubular member 20 to provide increased resistance to kinking between the adapter and the proximal tubular member. The strain relief can be formed of a polymeric material and extend distally along at least a length of proximal tubular member 20. The strain relief can be formed as a separate sleeve, or overmolded onto the proximal tubular member 20. A variety of materials can be used for the strain relief including polymers such as but not limited to FEP, PTFE, polyamide, and PEEK, and metals such as but not limited to stainless steel, and nitinol, e.g., spring.

The method or structure for joining proximal tubular member 20 to intermediate tubular member 22 will depend upon the materials used. For example, adhesive, welding, fusion, RF bonding, shrinking, or other bonding techniques can be employed. Particularly, if the proximal tubular member is formed from metal and the adjacent tubular member is formed from a polymeric material, the polymeric tubular member can be joined to the metallic tubular member by utilization of a compression tool such as but not limited to a jaw press.

In one embodiment, proximal tubular member 20 is a hypotube made of metal, such as stainless steel, and intermediate tubular member is a polymer, for example polyamide such as nylon. In this embodiment, distal region 20b includes an outer surface having a bonding region defined by a roughened outer surface across a length of the proximal tubular member (not shown). The roughened outer surface can be prepared by for example grit blasting, chemical means including etching and leaching, laser ablation techniques, or knurling a portion of the outer surface known techniques. The bonding region can have a length of at least approximately 10 to 20 mm to facilitate securing an adjacent tubular member to proximal tubular member 20. The bonding region can be provided at the distal end of the proximal tubular member 20 or, if desired, can be spaced proximal from the distal end. In further accordance with this embodiment, proximal region 22a of intermediate tubular member 22 can be configured to overlap at least a portion of the bonding region disposed on the outer surface of proximal tubular member 20. For example, and not limitation, intermediate member can overlap the entire length of the bonding region defined by the roughened surface or a portion thereof.

Figure 2:
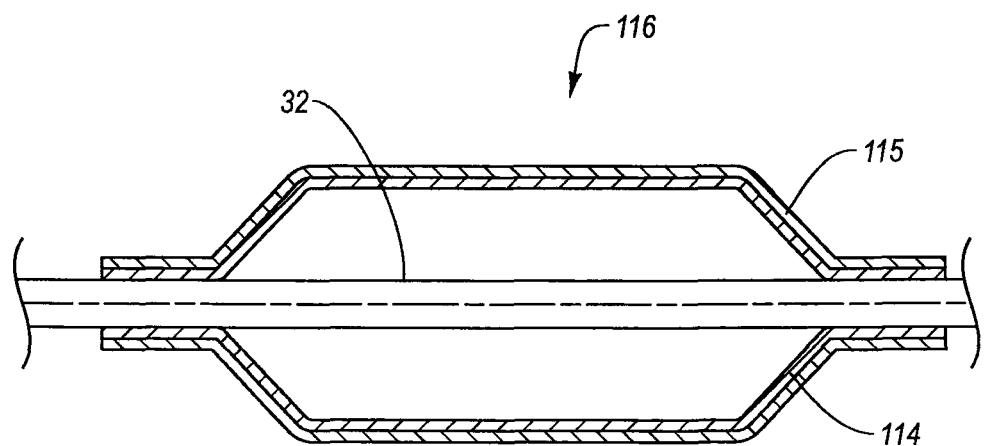
FIG. 2 is a cross-sectional view of an inflatable member in accordance with the present invention.

Distal region 20b is secured to an adjacent tubular member, such as intermediate tubular member 22, as depicted in FIGS. 1 and 2, by suitable structure or method. As shown schematically in FIG. 1, proximal end region 22a of intermediate tubular member 22 can be configured to form a lap joint such that proximal end region 22a includes a proximal end that overlaps at least a portion of the distal end region 20b of proximal tubular member 20.

Similarly, it is not required that the bond securing proximal tubular member to intermediate tubular member have a length equivalent to the length of the roughened surface. For the purpose of illustration and not limitation, the proximal region of intermediate member can be configured to overlap an entire length of the roughened surface, for example 10 cm, but have a bonding length of only about 1 cm in the proximal portion of the bonding region length. Accordingly, the intermediate tubular member 22 can be configured to bond to only a portion of the bonding region that is proximate a distal end the bonding region.

Alternatively, the proximal end of intermediate tubular member 22 can be configured to form a butt joint with the distal end of proximal tubular member 20, if desired. In this manner, a polymeric sleeve can be disposed over the junction defined by the butt joint to assist securing the proximal tubular member 20 to the intermediate tubular member 22, if necessary.

A variety of bonding techniques may be utilized to secure intermediate tubular member 22 to the bonding region of proximal tubular member 20. For example, and not limitation, fusion bonding, adhesive, welding, shrinking, and the like can be used.

A variety of materials can be used for proximal tubular member 20. Proximal tubular member 20 can be formed at least in part of a suitable metallic material, such as a metallic hypotube. For example, and not limitation, various metals can be used including stainless steel, nitinol, and other metal alloys. If stainless steel is used, austenitic stainless steel can be used.

In accordance with another aspect of the invention, the proximal tubular member 20 can be made of a pure carbon material, polymeric material, fiber reinforced materials such as carbon fiber reinforced material, glass fiber reinforced material, boron fiber reinforced material, Kevlar, metal or metal alloy. The metal or metal alloy can be MRI compatible, such as but not limited to niobium, tantalum, tungsten, or any variety of other paramagnetic metals. The use of such materials having sufficiently high compressive strength for proximal tubular member 20 is particularly advantageous to enhance pushability and provide kink resistance for rapid-exchange applications. If desired, the proximal tubular member 20 can further include a lubricious coating, such as a polytetrafluoroethylene or an HDPE coating. Alternative lubricious materials can be used, however, as known in the art. The proximal tube can also be coated with a hydrophilic or a hydrophobic coating to reduce friction, for example and not limitation, the hydrophobic coating can be silicone coating or the like, and the hydrophilic coating can be a polyvinylpyrrolidone or polyacrylamide coating.

Proximal tubular member 20 can also be formed of suitable polymeric material such as PEEK or other relatively stiff polymeric material. Alternatively, if desired, less stiff polymeric materials can be used and the desired stiffness can be achieved by utilizing a stiffening member positioned within the tube. Alternatively, proximal tubular member 20 can be formed of a composite member or formed member comprising a fabrication of different materials, such as reinforced polymer materials, or an extrusion or pultrusion of different polymers, if desired. The composite member or formed member can also be formed by a dip molding process, in which a mandrel is dipped into a polymer material, which is dissolved in a suitable solvent, dried, and then re-dipped into another polymer material to form a multi-layered polymeric composite or formed member. As yet another alternative, the composite member or formed member can be formed by applying a second polymeric tube about a first polymeric tube, applying a shrink tubing about first and second polymeric tube assembly and heating the assembly to fuse the first and second tubular members to each other. For each process for forming the composite or formed member described above, the outer surface of the inner polymeric tube can be roughened by mechanical or chemical means to improve the bond between the inner and outer tubular members. For example, the outer surface can be roughened by mechanical means including grinding, knurling, sandblasting, or laser-ablation, or chemical means including etching and leaching.

The composite member can also include a polymeric tubular member loaded with particles of a different polymer. For example and not limitation, a PEEK or polyimide tubular member can be loaded with PTFE particles. In this manner, the PTFE particles and/or a mandrel can be electrostatically charged such that an attractive force, e.g., electrostatic force causes an acquaintance between the PTFE particles and the PEEK tubular member. The PTFE particles can be secured to the PEEK tubular member for example by dip molding or over-molding techniques as known in the art. Alternatively, a polymeric outer layer, such as nylon tube, can be applied to the PTFE loaded tubular member to form a multi-material, multi-layer composite tubular member. As yet another alternative, the proximal tubular member can be a fiber-reinforced composite material such as fiber-reinforced resin material including but not limited to carbon reinforced material, glass reinforced material and boron reinforced material, or a liquid crystal reinforced material. Further, to achieve suitable stiffness of the proximal tubular member, a polymeric tubular member can include a metallic element disposed in the inner lumen of the polymeric tubular member, as will be discussed further below.

Generally, the proximal tubular member 20 can have a length of about 100 to about 115 cm. For example and not limitation, the proximal tubular member can be configured to have an outer diameter approximately 0.70 mm and an internal diameter of about 0.52 mm. However, as known in the art, the length and dimensions of the proximal tubular member can be varied depending on the size and location of the lumen(s) to be traversed by the catheter 100. For example, the proximal tubular member can be configured to have smaller dimensions, e.g., outer diameter and internal diameter, if the catheter is used to treat vessels in the brain or extremities of a patient. Furthermore, the proximal tubular member can be configured to have dimensions suitable for non-vascular applications, such as but not limited to those involving the urethra, esophagus, and/or intestine.

Intermediate tubular member can include a distal end region 22b, and can further include lumen 22c defined between distal end region 22b and proximal end region 22a. As previously mentioned, proximal end region 22a is secured to at least a portion of proximal tubular member 20, for example, at a bonding region defined by a roughened outer surface. Lumen 22c is thus in fluid communication with lumen 20c.

A variety of materials can be used for intermediate tubular member 22. For example, intermediate tubular member 22 can be made from any suitable polymer material such as polyamide, PEEK, PEBAX®, PTFE, PVDF, polyimide, polyethylene, polyester, polyurethane, or liquid crystal polymers of various suitable densities. As a further exemplary alternative, intermediate tubular member 22 can be a composite member or formed member comprising a fabrication of several different materials. For example and as described above in detail, the composite or formed member can be made by extrusion or pultrusion of different polymers, if desired. Alternatively, the composite member can be formed by dip molding, applying a first polymeric tubing within a second tubular member and fusing the assembly. Alternatively, the composite member can be formed by over-extruding a polymeric material over the tubular member to achieve a composite member or by a loading the polymer tubular member with particles of a different polymer, e.g., PEEK or polyimide tubular member loaded with PTFE particles, as described above. As yet another alternative, the intermediate tubular member can be formed from a fiber-reinforced material, such as fiber-reinforced resin material, e.g., carbon, glass, aramid, boron, or a liquid crystal reinforced material.

The dimensions of the intermediate tubular member 22 will depend upon the intended application. For example, for a cardiovascular catheter, the intermediate tubular member 22 can have a length of at least approximately 10 cm, although a greater length can be used to accommodate an overlap joint with the proximal tubular member 20. For example, and not limitation, the intermediate tubular member can have an outer diameter of approximately 0.85 mm and an inner diameter of approximately 0.70 mm. However, as will be recognized in the art, the intermediate tubular member 22 can be configured with alternate lengths and dimensions, if desired.

In further accordance the invention, and as demonstrated in FIG. 1, catheter 100 can further include a distal tubular member 24. Distal tubular member 24 has a proximal end region 24*a*, a distal end region 24*b*, and lumen 24*c* therebetween, and extends distally from intermediate tubular member 22 to distal section 106. The distal shaft lumen 24*c* is in fluid communication with lumen 22*c* of intermediate tubular member 22. Accordingly, an inflation lumen can be defined across a substantial length of catheter 100. If both are provided, intermediate tubular member 22 and distal tubular member 24 together thus define the intermediate section 104 of the catheter 100.

As shown in each of FIG. 1, a proximal end region 24*a* of distal tubular member 24 can be secured to at least a portion of distal region 22*b* of intermediate tubular member 22, as well as to at least a portion of a guidewire tube 30.

A variety of materials and dimensions can be used for distal tubular member 24. Indeed, if both an intermediate tubular member and a distal tubular member are provided, the two members can be formed of the same material and substantially the same cross section dimensions for uniform stiffness and flexibility, or even formed together as a single piece. Alternatively, the distal tubular member 24 can be formed of a different material and/or dimensions to vary flexibility along the length of the catheter. For example, distal tubular member 24 can be made from any suitable polymer material such as polyamide, PEEK, PTFE, PVDF, PEBAX®, polyimide, polyester, polyurethane, liquid crystal reinforced polymer, or polyethylene of various suitable densities. As a further exemplary alternative, distal tubular member 24 can be a composite member or formed member comprising a fabrication of several different materials, such as a co-extrusion or pultrusion of different polymers. Alternatively, the composite or formed member can be made by the dip molding process, polymer loading process, or by fusing first and second tubular members to each other, as described in detail above. Alternatively, the distal tubular member can be a fiber-reinforced material such as fiber-reinforced resin material, e.g., carbon, glass, aramid, or boron, or liquid crystal reinforced material.

The dimensions of distal tubular member 24 will depend upon the intended application. For example, for a cardiovascular catheter, the distal tubular member 24 can have a length of approximately 10 to 30 cm. In another configuration, the distal tubular member 24 can have a length of approximately 21 to 23 cm. For example, and not limitation, the distal tubular member can have an outer diameter of at least approximately 0.98 mm and an inner diameter of at least approximately 0.82 mm. However, as will be recognized in the art, the distal tubular member 24 can be configured with alternate lengths and dimensions, if desired. For example, for an endovascular application, the distal tubular member can have an outer diameter of at least approximately 0.4 mm and an inner diameter of at least approximately 0.2 mm.

In an alternate construction, catheter 100 can have proximal tubular member 20 extend distally from adapter 110 directly to distal tubular member 24. By way of further example, distal tubular member 24 of catheter 100 can be attached directly to the proximal tubular member 20 without an intervening intermediate section 22, such that distal tubular member 24 has a proximal region secured to the bonding region of proximal tubular member 20. In this manner, the proximal region 24*a* of distal tubular member 24 can be in an overlapping configuration with the distal region 20*b* of proximal tubular member 20 to define an overlapping region. The overlapping region can have a length of approximately 10 cm. Such a device can further improve pushability of catheter 100 and prevent kinking.

In accordance with another aspect of the invention, the elongate main body of the catheter 100 can include a feature for performing a diagnostic, an interventional, or a therapeutic procedure or treatment. This feature can be disposed at least partially at the distal section 106 of the catheter 100. For example, and for purposes of illustration and not limitation, as embodied herein and as depicted in FIG. 1, the elongate main body can further include an inflatable member 114 disposed along a length of the catheter 100. The inflatable member has a proximal end 114*a*, a distal end 114*b*, and an inflation chamber 114*c* bounded by a surface of inflatable member 114. Inflatable member 114 can be made from a variety of materials. For purpose of illustration and not limitation, inflatable member 114 can be made from a polyether block amide ("PEBA"), polyamide, polyurethane, PET, PE, PTFE, polyester, composite materials, or a variety of other materials, including blends. Alternatively, the inflatable member can be made from a polyhydroxyalkanoate including but not limited to poly-4-hydroxybutyrate, available from Tepha Inc., Cambridge, Mass. Inflatable member 114 can be attached to the distal tubular member 24 of catheter 100 by any of a variety of suitable bonding techniques, such as adhesive, fusion, welding, or other technique known by one skilled in the art. Thus, if inflatable member 114 is made of nylon, it is advantageous for distal body portion 24 to be made of a material compatible for a welded or fusion bond therebetween. For the purpose of illustration and not limitation, the inflatable member can be welded to the distal body portion using light energy, adhesive, or welding, e.g., heat welding, ultrasound welding, inductive welding, rotation welding, and the like.

In accordance with a further aspect of the invention, catheter can include a first guidewire lumen defined along a length of the catheter and a second lumen defined proximal to the first guidewire lumen along a length of elongate main body of catheter.

For example, and with reference to FIG. 1, catheter 100 is provided with a first guidewire tube 32 having a first guidewire lumen defined therethrough. The first guidewire lumen 32*c* accordingly can be provided with a proximal guidewire port 32*a* and a distal guidewire port 32*b* in fluid communication therewith. Similarly, the catheter 100 is provided with a second guidewire tube 30 having a second guidewire lumen defined therethrough. The second guidewire lumen 30c accordingly can be provided with a proximal guidewire port 30a and a distal guidewire port 30b in fluid communication therewith.

As embodied herein, the first guidewire lumen 32c is disposed along the distal section 106 of the catheter. For example, if an inflatable member 116 is provided, first guidewire lumen 32c extends through the inflatable member with the distal guidewire port 32b located distal the inflatable member and the proximal guidewire lumen located proximal the inflatable member. In an embodiment, inflatable member 116 is positioned on the elongate main body of catheter 100 equidistant between the proximal guidewire port 32a and distal guidewire port 32b, or the distal end of the tip 70, if provided. However, inflatable member 116 can also be placed closer to one port or the other, if desired.

Furthermore, and as embodied herein, the second guidewire lumen 30c is disposed proximal to and spaced from first guidewire lumen 32c. That is, distal guidewire port 30b of second guidewire lumen 30c is spaced proximal from proximal guidewire port 32a of first guidewire lumen 32c. A guidewire inserted distally through distal guidewire port 32b therefore will exit the catheter at proximal port 32a. As illustrated in FIG. 1, proximal guidewire port 32a of first guidewire lumen 32c can be axially aligned with distal guidewire port 30b of second guidewire lumen 30c. Advantageously, this arrangement provides an operator with an option to feed guide wire 60 solely through lumen 32c of first guidewire tube 32, as mentioned above or alternatively, feed guidewire 60 through each of first guidewire lumen 32c and second guidewire lumen 30c of second guidewire tube 30.

In an embodiment of the invention, at least the first guidewire lumen 32c is defined by a first guidewire tube 32. The first guidewire tube 32 embodied herein, is joined at its distal end region to the distal end of inflatable member 116 by conventional bonding techniques as depicted in FIG. 1. To anchor the proximal end region of first guidewire tube 32, and in accordance with another aspect of the invention, a circumferential slit is formed in the wall of distal tubular member 24. The wall on the proximal side of the circumferential slit is urged inward, such that the proximal end region 32a of first guidewire tube 32 extends through the slit with the wall of the distal tubular member substantially surrounding the first guidewire tube 32 as depicted in FIG. 6. A reinforcement filler or tube can be provided proximate the slit to anchor, seal and strengthen the joint between the tubular members.

The second guidewire lumen can be formed or defined by a separate tubular member disposed along a length of distal tubular member 24, or can be defined by the distal tubular member 24, itself, as described further below. If formed of a separate tubular member, the second guidewire tube can be anchored at its distal end region to distal tubular member 24 in a manner similar to that of the proximal end region of the first guidewire tube.

Particularly, and as depicted in FIG. 1 in accordance with either aspect of the invention, distal tubular member 24 further includes gap 24d along its length. Gap 24d is in fluid communication with the exterior of catheter 100. For purpose of illustration and not limitation, gap 24d can be constructed by placing two circumferential slits through the wall of distal tubular member 24 to define a flap region. The flap region is depressed toward lumen 24c of distal tubular member 24. Further, and as schematically shown in FIG. 1, the depressed flap region of distal tubular member 24 is disposed between a first guidewire tube 32 and a second guidewire tube 30. As schematically shown in FIG. 1, second guidewire tube 30 is disposed proximal to gap 24d and first guidewire tube 32 is disposed distal to gap 24d. Advantageously, gap 24d allows fluid communication between the exterior of catheter 100 and both the distal guidewire port 30b of second guidewire lumen 30c, and the proximal guidewire port 32a of first guidewire lumen 32c. Further, and as schematically depicted in FIG. 8, gap 24d provides an exit for a guidewire 60 disposed in the first guidewire lumen 32c, if desired.

As previously stated, a filler material or reinforcement tube 28 can be placed below the gap 24d to strengthen the region proximate the joints. If provided, a mandrel can be inserted during fusion of the members to ensure an inflation lumen is maintained. Additionally, if a stiffening element is provided in the lumen of the tubular member, the filler material provides added material to the sidewall of the tubular member so that the stiffening member does not disrupt the sidewall of the tubular member when the catheter is manipulated during use or during assembly.

The proximal end region of the second guidewire tube, if provided as a separate member, can be secured or anchored in a variety of different manners. For example, and as embodied herein, the proximal end region of second guidewire tube 30 can be secured between the distal end region 22b of intermediate tubular member 22 and the proximal end region 24a of distal tubular member 24 as depicted in FIG. 1. In an embodiment, the distal end region 22b of intermediate tubular member 22, as depicted in FIG. 1, can further include a longitudinal recess such that at least a portion of second guidewire tube 30 is nested within the longitudinal recess of the intermediate tubular member 22. For the purpose of illustration and not limitation, the longitudinal recess can be formed by necking down a distal region of the intermediate tubular member 22 or forming a dimple in of the intermediate tubular member.

With the second guidewire tube 30 positioned between the overlapping interface of the intermediate tubular member 22 and the distal tubular member 24, the structure can be fused together to form a joint therebetween. If desired, a filler material or reinforcement tube 26 can be disposed proximate the joint as depicted in FIG. 1. A mandrel can be located temporarily across the joint when the structure is fused together to define an inflation lumen 22 therethrough.

Alternate constructions for the second guidewire lumen, and the corresponding region, are describe further below.

The material of construction and dimensions for the guidewire lumens will depend upon the intended application. For example, for a cardiovascular catheter, each of the first and second guidewire lumens can be constructed from any suitable polymer such as nylon, PEEK, HDPE, polyimide, PTFE, or PTFE loaded polyimide, polyurethane, polyester, liquid crystal polymer, and the like, including blends or composites thereof. Further, each of the lumens can be made of one or more extruded or pultruded materials, including multilayered co-extrusions or pultrusions, or monolayered material, as discussed below. The first guidewire lumen can have a length of at least approximately 1 cm, and second guidewire lumen can have a length of at least approximately 17 cm.

Catheter 100 can be configured to have proximal guidewire port 30a approximately 10 to 30 cm proximal to distal tip 70 of catheter 100. In another configuration, the proximal guidewire port 30a can be about 20 to 30 cm proximal to distal tip 70. Accordingly, catheter 100 can be configured such that guidewire 60 can be disposed through first guidewire tube 32 and exits catheter body at guidewire port 32a of first guidewire tube 32 and then re-enters catheter body 100 at distal port 30b of second guidewire tube 30. Guidewire 60 extends proximally through second guidewire lumen 32c to proximal port 30a.

Generally, first guidewire tube 32 is shorter in length than second guidewire tube 30. For example and not limitation, first guidewire tube 32 can have a length of at least approximately 3 to 4 cm; although generally is dependent at least on the length of inflatable member 114. Second guidewire tube generally has a length of approximately 10 to 30 cm, but can have a length of about 21 to 23 cm or some other length greater or lesser than 10 to 30 cm, depending on the length of the inflatable member 114. In one configuration, the outer diameter of first and second guidewire tubes, 32 and 30, respectively, are approximately about 0.4 mm, and the inner diameter of first and second guidewire tubes, 32 and 30, respectively, are approximately about 0.2 mm. However, it should be recognized that each of first guidewire tube 32 and second guidewire tube 30 can have any suitable length and dimension, as desired.

A variety of materials can be used to form first guidewire tube 32 and second guidewire tube 30. For example and not limitation, either first guidewire tube 32 or second guidewire tube 30 can be formed of polymers such as polyamide, PEEK, HDPE, PEBAX®, Polyurethane, and the like, including blends thereof. Alternatively, either the first or second guidewire tube can be formed from a composite or formed member. For example and not limitation, either guidewire tube can be made of one or more extruded or pultruded materials, dip molded materials, polymeric loaded materials, or shrink fitted materials, as described above. As yet another alternative, either the first or second guidewire tube can be formed of fiber reinforced materials.

In one embodiment, second guidewire tube 30 is formed of a multi-layered co-extrusion, and first guidewire tube 32 is formed of a monolayer polymeric material. For example and not limitation, second guidewire tube 30 can be formed of at least a two-layer material including an inner polymeric layer and an outer polymeric layer.

The inner layer can be a lubricious material and facilitate gliding of guidewire 60 through guidewire lumen. Alternatively, the inner material can have a lubricous coating, for example, with a silicone coating.

In one embodiment, the second guidewire tube is formed of an inner layer including HDPE and an outer layer including a polyamide, such as nylon. However, alternative materials can be used for either the inner layer or the outer layer as known in the art. For example, the inner layer can alternatively be formed from materials such as polyimide, PTFE, or PTFE loaded polyimide and the outer layer can be formed from materials including nylon, nylon copolymers including Pebax®, Hytrel®, polyolefin, polyurethane, and blends thereof. Alternatively, other suitable materials can be used as known in the art.

The inner layer can be secured to the outer layer by various suitable methods and structures, which depend on the particular selection of the inner layer material and the outer layer material, as known in the art. For example, the inner layer can be secured to the outer layer by a mechanical bond, chemical bond, or other bonding means such as mechanical friction fit. For example and not limitation, a lubricious inner layer of HDPE is mechanically bonded to an outer layer of nylon.

As mentioned above, guidewire tube 32 can be formed of a monolayer polymeric material. As depicted in FIG. 1, distal end of inflatable member 114 is secured to first guidewire tube 32. Accordingly, the particular material selected for the first guidewire tube 32 should be compatible with the material selected for the inflatable member 114. First guidewire tube 32 can be formed of a monolayer of nylon or PEBA material, and inflatable member 114 is a nylon balloon, such that a fusion bond can be formed therebetween. Alternatively, the inflatable member can be adhesively bonded to the first guidewire tube. Alternatively, both members can be formed of a polyamide like Nylon or PEBA material. Furthermore, the first guidewire tube can be formed of a multi-layer tubular member, if desired.

In accordance with another aspect of the invention, the first guidewire lumen and the second guidewire lumen can be provided in direct communication with each other, such that no gap is formed therebetween.

In another embodiment, the first guidewire tube 32 is formed of a monolayer material capable of being bonded to the material of the inflatable member, such as nylon, PEBA or a nylon blend. The second guidewire tube 30 can be formed of a multi-layer member, such as a two-layer co-extruded tube. For purpose of example and not limitation, the two-layer guidewire tube 32 can include an inner polymeric layer and an outer polymeric layer. The inner layer can be made of a lubricious material to facilitate gliding of the guidewire through the lumen. Additionally, the inner layer can include a lubricious coating, for example, a silicon coating. The outer layer can be made of a material that facilitates bonding with adjacent components, such as by fusion or adhesives. In one configuration, the inner layer can be made of HDPE material with the outer layer of nylon or PEBA material mechanically bonded thereto. Additional and/or alternative materials and layers can be provided as needed or desired, as previously described.

The proximal end of the first guidewire tube is sealed to the distal end of the second guidewire tube, such as by a butt joint, a lap joint, or a surrounding sleeve joint using adhesives, welding, fusion or the like. As embodied herein the joint between the first and second guidewire tubes is located between the distal port 32b and the proximal port 30a, and can be located along the distal section of the main body portion. For example, the transition from the two-layer tube to the monolayer tube can be disposed proximate the bonding junction of the inflatable member 116 to the distal tube 24.

Alternatively, and as previously noted, the first guidewire tube and the second guidewire tube can be constructed as a single piece member. For example, the first and second guidewire tubes can be formed of the same materials or can be extruded or molded of different materials that transition along the length of the single tubular member.

In further accordance with the invention, distal tip 70 can be secured to first guidewire tube 32. As depicted, distal tip 70 is in an overlapping configuration with the distal end of first guidewire tube 32. In one embodiment, distal tip is configured to abut the distal end of inflatable member 114. Alternatively, however, distal tip 70 can be configured to overlap the distal end of inflatable member 114. The distal tip 70 can be secured to the distal end of first guidewire tube by heat welding. However, other methods can be used such as using adhesive's, or the like.

A variety of materials can be used to form distal tip 70. The distal tip 70 can be formed of a material having a durometer less than the durometer of the distal tubular member 24. For example and not limitation, distal tip 70 can be formed of polyamides, including nylon, polyether block amide, high density polyethylene, polyurethane, polyesters, including HYTREL. The particular selection of the material for the distal tip 70, however, is depending on the desired application of catheter 100.

As previously noted, the second guidewire lumen can be formed by a second guidewire tube or by other construction. For example, FIG. 1 depicts a catheter with second guidewire lumen 30c defined by second guidewire tube 30. The proximal guidewire port 30a is defined wholly by the proximal end region of second guidewire tube 30 due to the joint configuration previously described. In this manner, and by using a tubular member with a lubricious inner layer, placement of the catheter relative to the guidewire can be enhanced.

Between the proximal guidewire port 30a and the distal guidewire port 30b, the second guidewire lumen 30c can be disposed either in a coaxial relation or a side-by-side relation with the inflation lumen 24c, or even a hybrid of the two.

As described above the catheter 100 includes and inflatable member 116 disposed adjacent to the distal end of the catheter 100, wherein the inflatable member is composed of a composite structure.

Figure 3:
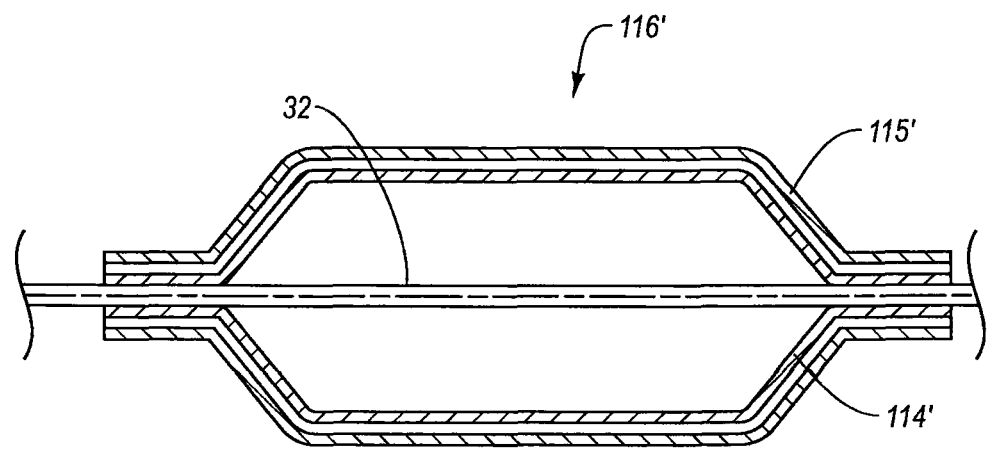
FIG. 3 is a cross-sectional view of an alternative embodiment of an inflatable member in accordance with the present invention.

Referring now to FIGS. 2 and 3 there are shown exemplary embodiments of inflatable members in accordance with the present invention. The inflatable member 116 in accordance with the present invention can be constructed as a composite member comprising at least two materials.

As shown in FIG. 2, the inflatable member 116 as show is constructed of an outer material 115 and an inner material 114. The outer material 115 can be a semi-compliant or fully compliant material. Examples of suitable materials include Polyurethane, PET, Nylon 11, Nylon 12, PEBAX as well as blends thereof. The inner material 114 can be constructed of a non-compliant material such as a polyamide or a polyvinyl alcohol.

The composite balloon assembly 116 shown in FIG. 2 is constructed utilizing a dual extrusion process, wherein the two different materials are co-extruded to form a tubular member from which the composite balloon 116 may be constructed. This could also be achieved by extruding two separate tubes and disposing one tube inside another a bond between the two tubes could be achieved during the balloon forming process. Additionally, an outer tubular member may be formed, wherein the inner tubular member is formed by coating the inner surface of the outer tubular member with a material configured to form the inner tubular member.

Referring now to FIG. 3 there is shown an alternative embodiment of an inflatable member 116' in accordance with the present invention. As described above the inflatable member 116' is constructed as a composite member having an inner balloon member 114' and an outer balloon member 115'. Unlike the embodiment shown and described with reference to FIG. 2, the inflatable member 116' of the present invention is constructed by disposing an inner inflatable member 114' within an outer inflatable member 115', wherein the inner inflatable member 114' can be a non-compliant inflatable member and the outer inflatable member 115' can be a semi-compliant or a compliant inflatable member.

In use, the catheter 100 is disposed within a vessel or lumen to be treated by advancing at least a portion of the catheter over a guidewire. After placing the inflatable member 116 of the catheter at a location to be treated, a first inflation fluid is utilized to inflate the inflatable member 116. As previously described, it is preferred to initially utilize a non-compliant inflatable member to treat a lesion; therefore the inflatable member 116 will be inflated with a gas, such as CO2, etc. wherein the gas inflates the inflatable member 116. Instead of a gas, a liquid could be used that does not solve the inner balloon material, e.g. a non-polar solvent. The inflatable member 116 will have non-compliant properties because the inner inflatable member 114, 114' is constructed of a non-compliant material. After initially treating the lesion with the non-compliant inflatable member, the inflation medium utilized to inflate the inner inflatable member 114, 114' is removed and replaced with a second inflation medium. In one configuration, the second inflation medium is a liquid. The liquid causes the inner inflatable member 114, 114' to dissolve, pin-hole or otherwise breakdown. The inner inflatable member 114, 114' can lose its mechanical properties and weakens when in contact with the inflation fluid. Thus, the inner inflatable member 114, 114' looses its non-compliant characteristics, wherein the outer inflatable member 115, 115' is then inflated by the inflation fluid. The outer inflatable member 115, 115' having semi-compliant or compliant characteristics allows for oversizing of a vessel.

Suitable inflation liquids include water of other aqueous solutions that cause a breakdown in the properties of the inner inflatable member 114, 114'. The contact between the inflation liquid and the surface of the inner inflatable member can cause the change in mechanical properties of the inner inflatable member 114, 114'. The breakdown in mechanical properties of the inner inflatable member 114, 114' can be nearly instantaneous with contact with the inflation fluid, though longer times may be acceptable.

Although the present invention has been described in accordance with a balloon catheter, it is further contemplated that an endoprosthesis such as a stent may be radially disposed about and crimped onto the inflatable member 116,116' in accordance with the present invention, wherein the catheter 100 can be utilized to deliver a stent to a treatment size, then be utilized to upsize or oversize the stent and vessel without requiring removal of the catheter.

Further still, although the present invention has been described herein with reference to a "rapid-exchange" type of catheter, it is contemplated that the present invention may be embodied in the form of an "over the wire" catheter or a fixed wire catheter as known to those of ordinary skill in the art.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A balloon catheter comprising:
a shaft having a proximal end and a distal end; and
an inflatable member disposed adjacent the distal end of the shaft, the inflatable member comprising an inner inflatable member and an outer inflatable member disposed around the inner inflatable member, each of the inflatable members having different compliant properties
wherein the inner inflatable member is constructed of polyvinyl alcohol.

2. The balloon catheter of claim 1, wherein one of the inflatable members has non-compliant properties.

3. The balloon catheter of claim 2, wherein the other inflatable member has semi-compliant properties.

4. The balloon catheter of claim 2, wherein the other inflatable member has compliant properties.

5. The balloon catheter of claim 1, wherein the outer inflatable member is constructed of a material selected from the group consisting of Nylon 11, Nylon 12, and PEBAX.

6. The balloon catheter of claim 1, wherein the inner inflatable member is configured to break down when inflated with an inflation liquid.

7. The balloon catheter of claim 1, wherein the inner inflatable member is configured to break down when inflated with saline solution.

8. A balloon catheter comprising:

a shaft; and an inflatable member attached to the shaft, the inflatable member comprising an inner inflatable member and an outer inflatable member disposed around the inner inflatable member, the inner inflatable member having a lower compliant property than that of the outer inflatable member, wherein the inner inflatable member is configured to weaken, develop a hole, dissolve, or at least partially pass into solution by exposure to an inflation liquid, wherein the inner inflatable member is constructed of polyvinyl alcohol.

9. The balloon catheter of claim 8, wherein the outer inflatable member is constructed of a material other than polyvinyl alcohol.

\* \* \* \* \*